(12) United States Patent
Herold

(10) Patent No.: US 7,526,488 B2
(45) Date of Patent: Apr. 28, 2009

(54) PROCESSING METHOD FOR DATA WHICH IS COMBINED TO FORM A PLURALITY OF DATA RECORDS, USING A PLURALITY OF APPLICATIONS

(75) Inventor: Gerold Herold, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 889 days.

(21) Appl. No.: 10/463,531

(22) Filed: Jun. 18, 2003

(65) Prior Publication Data

US 2004/0040027 A1   Feb. 26, 2004

(30) Foreign Application Priority Data

Jun. 20, 2002   (DE)   ................ 102 27 560

(51) Int. Cl.
*G06F 17/30* (2006.01)
(52) U.S. Cl. .............. 707/100; 707/200; 717/174
(58) Field of Classification Search ........... 707/100, 707/102, 8, 104.1, 2
See application file for complete search history.

(56) References Cited

U.S. PATENT DOCUMENTS

| 4,805,099 | A | * | 2/1989 | Huber | .......... 707/102 |
|---|---|---|---|---|---|
| 5,293,615 | A | * | 3/1994 | Amada | .......... 707/4 |
| 5,522,066 | A | * | 5/1996 | Lu | .......... 707/1 |
| 6,088,706 | A | * | 7/2000 | Hild | .......... 707/202 |
| 2003/0088439 | A1 | * | 5/2003 | Grushka | .......... 705/2 |
| 2003/0140044 | A1 | * | 7/2003 | Mok et al. | .......... 707/10 |
| 2004/0019542 | A1 | * | 1/2004 | Fuchs et al. | .......... 705/32 |
| 2004/0034707 | A1 | * | 2/2004 | Royer | .......... 709/227 |

OTHER PUBLICATIONS

Panagiotis, Christias. *UNIXhelp for Users*. UNIX man pages: apropos (1), Man-cgi 1.15, 1994. URL: http://unixhelp.ed.ac.uk/CGI/man-cqi?apropos Viewed: Sep. 26, 2002.
NeoTool Development, LLC. Introduction to CCOW (Revised Jan. 25, 1999). NeoTool Development, LLC, 2002. URL: http://www.neotool.com/training/ccow Viewed: Sep. 26, 2002.

* cited by examiner

*Primary Examiner*—Cheryl Lewis
(74) *Attorney, Agent, or Firm*—Harness, Dickey & Pierce, P.L.C.

(57) ABSTRACT

A computer executes quasi-simultaneously a plurality of applications which process data combined to form data records. Only data of a single data record is processed at one time. If an application loads data of another data record, this is transferred to a central management component which forms a list of the applications in which descriptions of the functionalities which are executed by the applications are also stored. The management component causes the other applications to terminate the processing of the data of the first data record.

27 Claims, 6 Drawing Sheets

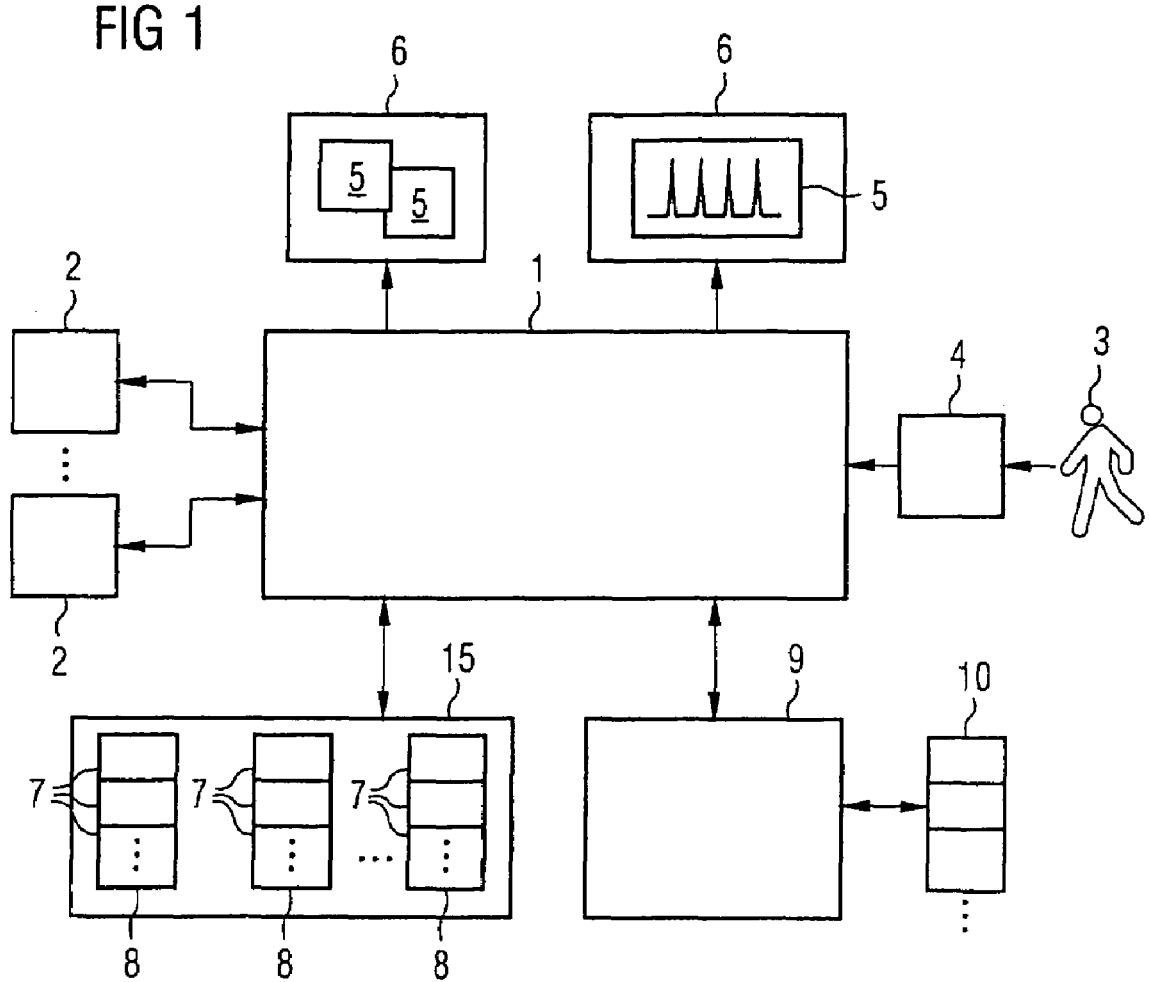

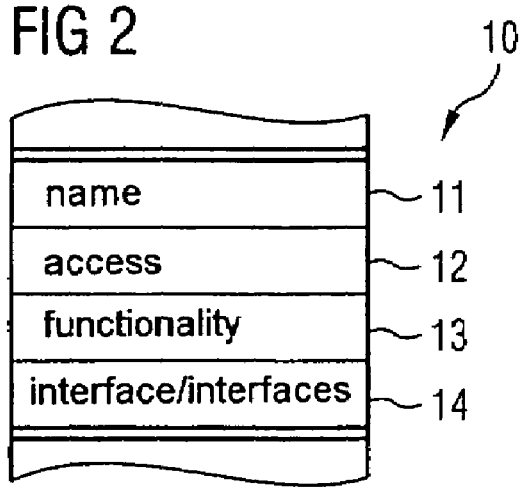
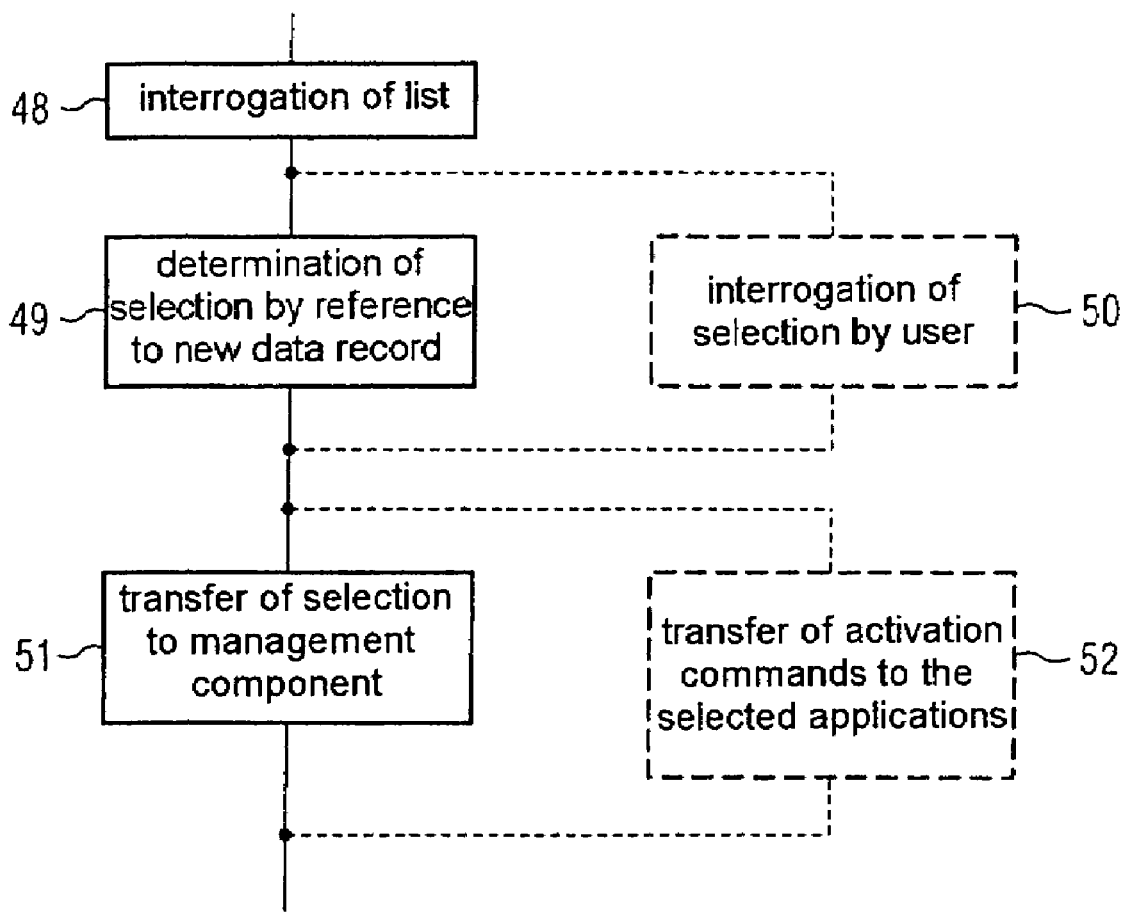

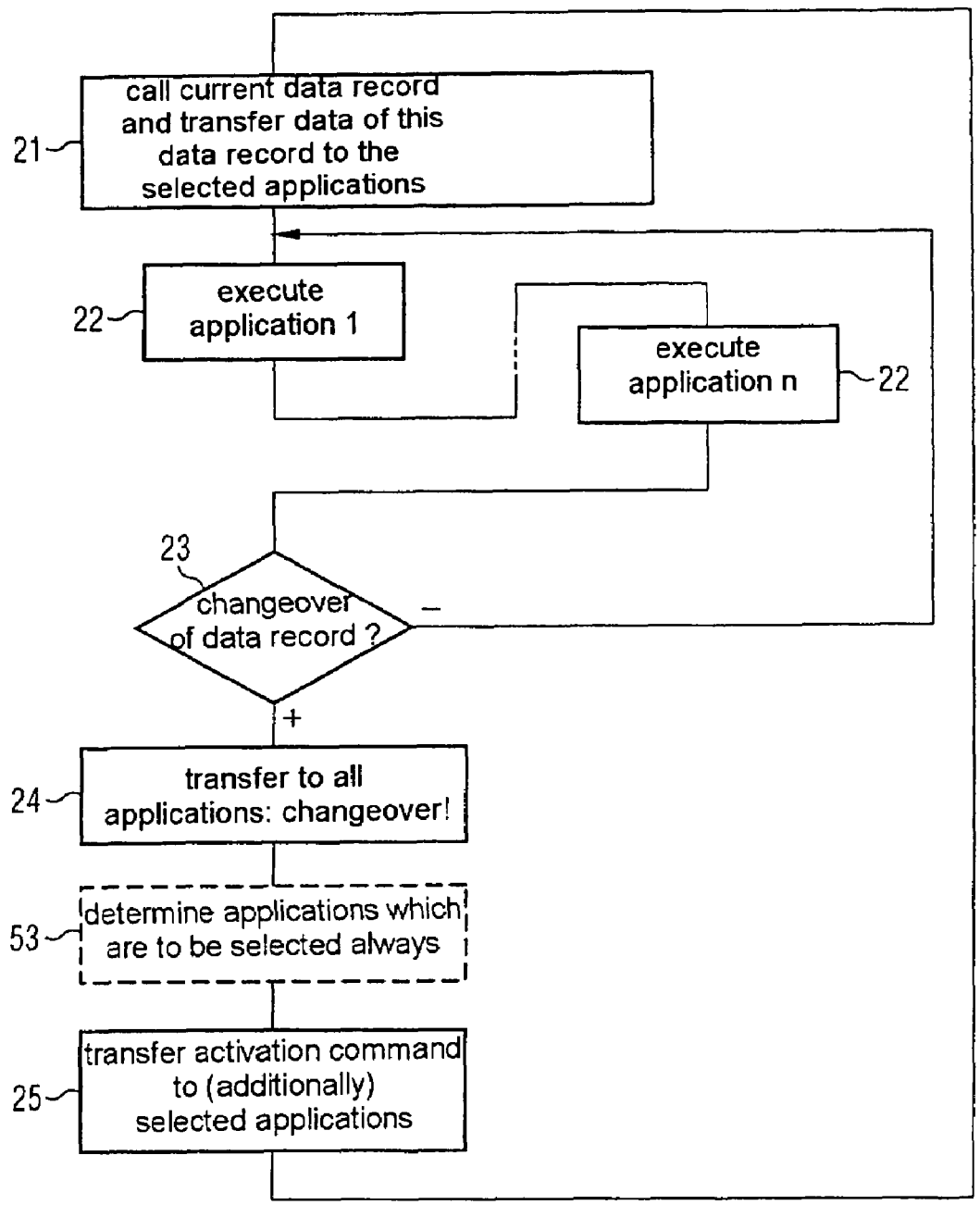

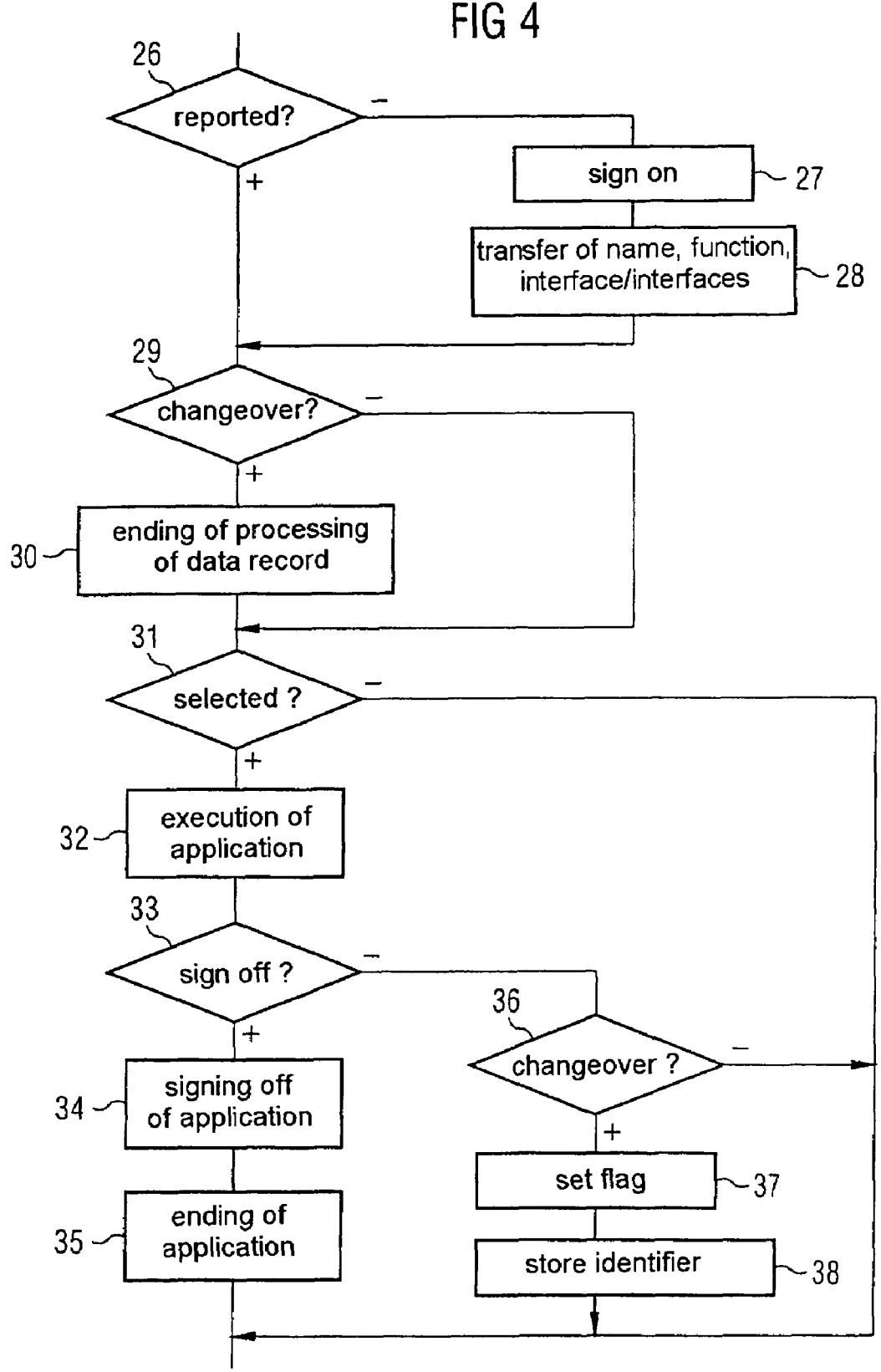

PROCESSING METHOD FOR DATA WHICH IS COMBINED TO FORM A PLURALITY OF DATA RECORDS, USING A PLURALITY OF APPLICATIONS

The present application hereby claims priority under 35 U.S.C. §119 on German patent application number DE 10227560.2 filed Jun. 20, 2002, the entire contents of which are hereby incorporated herein by reference.

FIELD OF THE INVENTION

The present invention generally relates to a processing method for data which is combined to form a plurality of data records, using a plurality of applications. The applications may be executed quasi-simultaneously by a single computer. Data which is assigned to a first data record may be processed by the applications at one time. The changeover of the data record when data of a second data record is loaded into one of the applications may be transferred to a central management component which is also executed by the computer and which forms a list of the applications. The central management component may cause the other applications to terminate the processing of the data of the first data record.

BACKGROUND OF THE INVENTION

Processing methods are known. Reference is made by way of example to the set of slides "Introduction to CCOW" from Neotool, which can be found at http://www.neotool.com/training/ccow/.

"UNIX man pages: apropos ( )" by C. Panagiotis, Man-cgi 1.15, 1994 discloses a function which searches through a set of database files, containing brief descriptions of system commands, for a keyword predefined for the function, and outputs the result.

It is known that a user on a desktop workstation uses a large number of different applications in order to perform a task which extends over more than one application. Such a workstation is referred to as a front end or client if access is made to central services or databases, which are referred to as backends or servers.

In order to be able to perform the task which extends over more than one application it is necessary to ensure that consistent data is used in all the applications. It is therefore necessary to ensure that the data items are identical and that data from the same data record is used in all the applications which are employed. In the medical area this refers to, for example, that person-related medical data of a patient, for example the date of birth or the case history, is kept in a consistent way in the various backends. In addition, it is necessary to ensure that data of the same patient is represented and processed in the front end applications. This is because errors may occur if, for example, a doctor is to diagnose a case and data of a different patient are represented in an application.

In order to ensure the consistency of data in the backend, it is necessary to perform a data reconciliation in the servers. Such a data reconciliation is usually referred to as backend integration.

In order to bring about the consistency of data in the front end, it is necessary to ensure that data of the same data record is processed in all the applications. This type of consistency is referred to as front end integration. The present invention relates only to this front end integration.

In order to process data of the same data record in all applications, what is referred to as the CCOW Standard (CCOW=clinical context object workgroup) has been defined. This Standard describes an application management system in which all the applications sign on to a central management component, which is referred to as the context manager. If a further data record is loaded into one of these applications, this application transfers unambiguous identifiers of the newly loaded data record to the context manager. The context manager is thus in a position to pass on this information to all the other signed-on applications. The applications can thus terminate the processing of the data of the data record which is being processed by them at a particular time, and load data of the new data record. However, in this method, the information about a new data record is always passed on to all the applications which are signed on at the context manager. A targeted selection of applications is not possible.

In the prior art it is also known to introduce what are referred to as extensions into individual applications. Here, each application can be inserted into a different application as an extension. The introduction of the extension brings about, for example, a menu entry or causes a button to be displayed in an operator control field. By appropriate inputting it is then possible for a user of the application to send data, in particular about a data record which is being processed by him at that time, to another application in a targeted fashion. The selection of the target application can also be automated if appropriate. For example, it is possible for an application to pass on automatically processed images for filming and archiving to a corresponding autofilming application if the application is expanded with a filming extension.

In order to interconnect all the applications to all the other applications in this concept, a very large number of extensions have to be configured. This is because the expenditure on mutual interconnection grows quadratically with the number of applications which have to be interconnected to one another.

In addition, what is referred to as an RIS system from Novius was connected to a platform software package Syngo at the RSNA 2001 in Chicago. A direct connection was formed between the two systems, that is to say Syngo and Novius exchanged data directly. Buttons were inserted into Novius from Syngo, and the user was able to activate functionalities in Syngo from Novius using these buttons. The functionality was transferred in the form of button bit maps and what is referred to as a tool tip. In this solution, only the user himself is in a position to select a specific functionality in Syngo. For the application of Novius, all the functionalities of Syngo are anonymous.

SUMMARY OF THE INVENTION

An object of an embodiment of the present invention is to develop a processing method of the generic type in such a way that applications which are appropriate and necessary for the processing of the data of the second data record can be selected in a targeted fashion in an easy way and with low expenditure. Such a selection is appropriate in particular because the amount of data in a data record may be very large in total, thus requiring a considerable amount of time to load into the applications.

An object may be achieved in that at least descriptions of the functionalities which are executed by the applications are also stored in the list. This is because a targeted, and nevertheless flexible selection of the individual applications is then possible for the user. However, the expenditure on making available the cross links between the applications no longer rises quadratically but then only linearly with the number of applications.

If descriptions of interfaces of the applications are also stored in the list, the processing method functions even better. This is because a direct communication of the applications with one another is then possible. If the applications sign on at the central management component when they start and sign off when they end, the list of applications is always up to date. Alternatively, or additionally, it is also possible for the applications to be entered into the list and/or removed from the list by a user of the computer via a user interface.

If, when there is a changeover of the data record, an activation command is transferred to selected applications of the applications, on the basis of which command the data of the second data record are to be processed and the nonselected applications do not begin processing data of the second data record, the data handling which occurs when the data record is changed over can be minimized.

It is possible for the central management component to determine the selected applications automatically by reference to the second data record. For example, the data record may contain an information item which indicates that it is a lung examination. In such a case, it is possible, for example, to dispense with representing heart data or blood fat values etc.

Alternatively, it is also possible for the selected applications of the central management component to be predefined by a user via a user interface. Although such a predefinition is (slightly) more costly, it is also particularly flexible.

It is also possible for the selected applications of the central management component to be predefined by the application which first loads data of the second data record. The application which first loads data of the second data record can perform the selection of the applications again itself, for example by reference to the second data record, in this context. It is also possible for the selected applications to be predefined to this application by a user via a user interface.

The transfer of the activation command can alternatively be performed by the central management component or by the application which first loads the data of the second data record.

If information indicating which applications are to be selected always is stored in the central management component, a default predefinition is possible. For example, it is possible to predefine that a filming or a reporting application is always selected.

If the central management component is designed as a work flow manager, then the process operates even better. If, on request, the central management component transfers the list of applications to the application which first loads data of the second data record, a particularly targeted selection of the applications which are to be selected is possible from the application. In particular, in such a case a user may make, for example, an alternative selection if a specific application which is actually desired by him is not present.

A typical application case of the processing method according to an embodiment of the invention is medical diagnosis and evaluation. The data records are therefore preferably person-specific medical data records.

BRIEF DESCRIPTION OF THE DRAWINGS

Further advantages and details emerge from the following description of an exemplary embodiment in conjunction with the drawings, in which, in a basic view:

FIG. 1 shows a block circuit diagram of a computer,

FIG. 2 shows a list, and

FIGS. 3-9 are flowcharts.

DETAILED DESCRIPTION OF THE PREFERRED EMBODIMENTS

Figure 5:
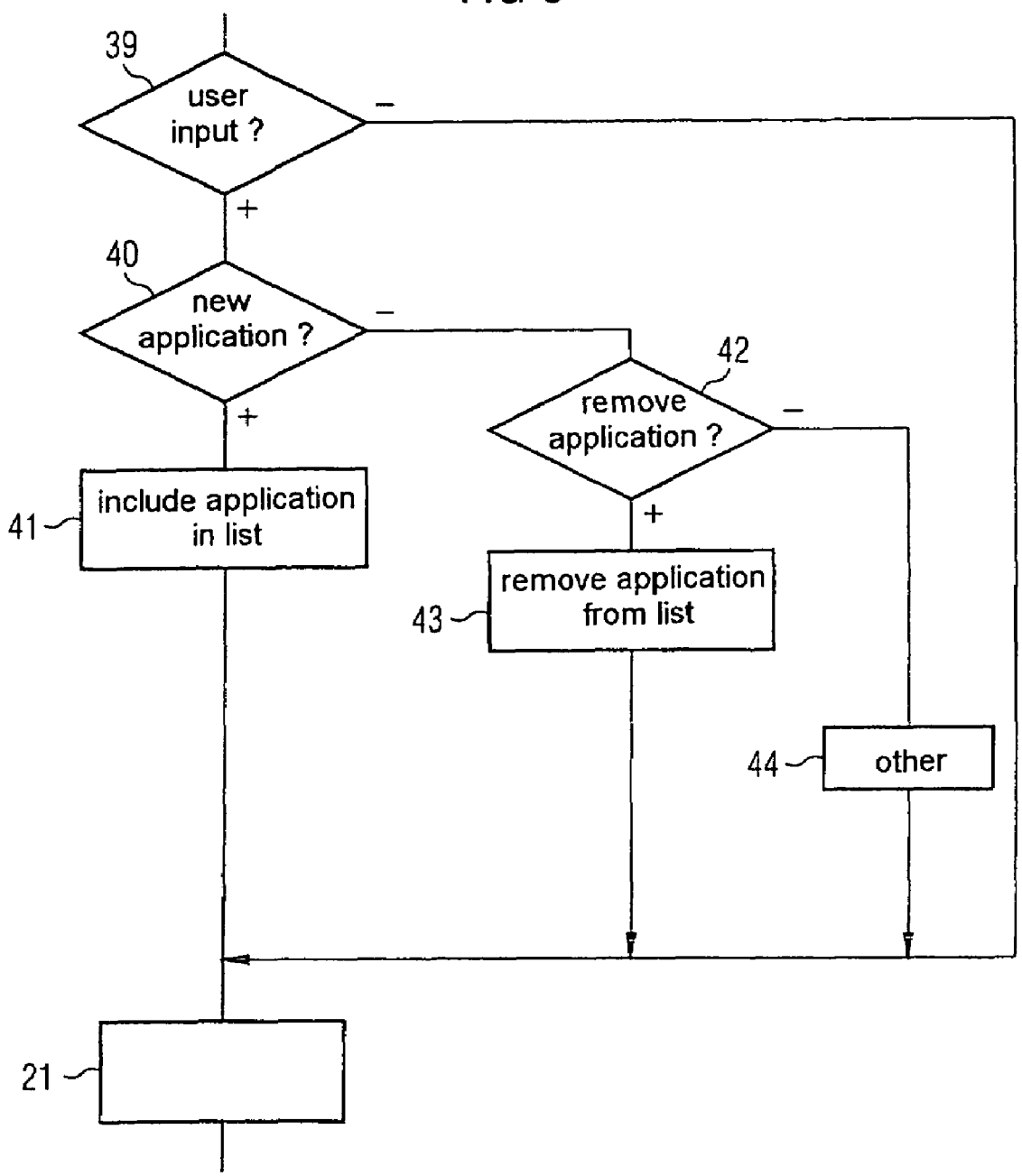

According to FIG. 1, a computer workstation has a computer 1. The computer 1 executes, under the control of an operating system (not illustrated)—a number of applications 2 quasi-simultaneously. Within the scope of the execution of the applications 2, they perform, inter alia, user inputs which are predefined to them by a user 3 via a user interface 4. The applications 2 also display outputs in windows 5. The windows 5 are displayed on VDUs 6.

According to FIG. 1, a plurality of VDUs 6 are assigned to the computer. A single window 5 is represented on one of the VDUs 6, and a plurality of windows 5 in a further of the VDUs 6.

The applications 2 also access data 7. The data 7 is combined to form data records 8. The data 7 may be, for example, person-specific medical data. For this reason, a heart beat curve is displayed by way of example in one of the windows 5.

Each data record 8 contains data 7 of a single person or a single patient. The data records 8 are therefore person-specific medical data records 8. All the data 7 of the same person are generally contained in a single data record 8. However, in an individual case, it is also possible for there to be a plurality of data records 8.

In order to ensure satisfactory interaction between the applications 2, it is necessary that only data 7 from the same data record 8 are processed by all the applications 2 at one time. For this reason, there is a central management component 9 which is also executed by the computer 1. It carries, inter alia, a list 10 of the applications 2. The central management component 9 is embodied as a computer program product 9 with which the computer 1 is programmed. According to FIG. 2, the list 10 contains, for each application 2, a name 11, an access 12, a description 13 of the functionality of the respective application 2 and a description 14 of the interface or interfaces of the respective application 2.

The method of operation of the central management component 9 is described in more detail below in conjunction with FIGS. 3 to 9.

According to FIG. 3, the central management component 9 firstly executes a step 21. In this step 21, the central management component 9 calls the data record 8 which is to be processed at that time from a data memory 15 and transfers data 7 of this data record 8 to selected applications 2. It is therefore embodied as a work flow manager. The selected applications 2 are executed in steps 22, if appropriate only for short time periods.

The applications 2 may load, inter alia, data 7 of a new second data record 8. In this case, a message is sent to the central management component 9 in a way which is to be described below (see FIG. 4).

The central management component 9 therefore checks, in a step 23, whether a data record changeover has taken place. If the data record 8 has not been changed over, the system jumps back to the steps 22. If, on the other hand, a changeover of the data record has taken place, the information indicating that such a changeover of the data record 8 has taken place, the information indicating that such a changeover of the data record 8 has taken place is transmitted to all the applications 2 in a step 24 by the central management component 9. The other applications 2 are therefore in a position to terminate the processing of the data 7 of the previously processed data record 8. The central management component 9 therefore causes the other applications 2 to carry out this termination. Finally, in a step 25, the central management component 9 transfers activation commands to the selected applications 2. More details will be given below on the way in which the applications 2 to be selected are determined, in conjunction with FIGS. 6 to 9.

During the processing, the applications 2 according to FIG. 4 firstly execute a step 26. In this step 26, the applications 2 check whether they have already signed on at the central management component 9. If this is not yet the case, they sign on in a step 27, and in a step 28 they transfer in particular their name, a description 13 of their functionality and a description 14 of their interface or interfaces to the central management component 9. Thus, for example, a filming application reports to the central management component 9 that it wishes to make available the service "filming". In addition, it transfers the necessary data and formats for this. If a different application 2 then wishes to use this service, it can determine from the central management component 9 whether the application "filming" is available. It can then communicate with this application 2 either directly or via the central management component 9, depending on the rest of the configuration of the method.

Otherwise, the system branches directly to a step 29. In the step 29, the applications 2 check whether a changeover of the data record 8 has been reported to them by the central management component 9. If this is the case, in a step 30 they end the processing of the data record 8 which has been previously processed by them. Otherwise they branch directly to a step 31.

In step 31, the applications 2 check whether they are selected applications 2. They therefore check whether they have received an activation command. If this is not the case, the respective application 2 will exit without further actions.

Owing to the direct exiting of the application 2 without further measures, only the processing of the original data record 8 is therefore ended. On the other hand, the new data record 8 is no longer loaded. If the application 2 is selected, a step 32 is firstly carried out. In this step 32, the actual processing of the data 7 of the respective data record 8 takes place.

Then, in a step 33, it is checked whether the application 2 is to be ended. If this is the case, the application 2 signs off at the central management component 9 in a step 34. The application 2 then ends in a step 35.

If the application 2 is not to be ended, it then checks, in a step 36, whether data 7 of a new data record 8 has been loaded in step 32. If this is the case, a flag is set in a step 37. In addition, an identifier of the newly called data record 8 is stored in a step 38. The flag and the identifier can be read by the central management component 9. As a result, the central management component 9 can, on the on hand, determine that a changeover of a data record has taken place and, on the other hand, identify and find the new data record 8.

In the method described in FIGS. 3 and 4, the applications 2 sign on and off automatically at the central management component 9. Alternatively, or additionally, it is however also possible according to FIG. 5 to carry out steps 39 to 44 between the steps 25 and 21 in FIG. 3. In this case, within the scope of the central management component 9, there is firstly an interrogation in step 39 to determine whether a user input was made for the central management component 9. Then, in a step 40 there is an interrogation to determine whether a new application 2 has been predefined. If this is the case, the new application 2 is included in the list 10 in a step 41. Alternatively, in step 42 it is checked whether an application 2 is to be removed. If this is the case, the application 2 is removed from the list 10 in step 43. Otherwise, a different reaction takes place in step 44.

In the embodiment according to FIG. 5, the applications are therefore entered into the list 10 or removed from it by the user 3 of the computer 1 via the user interface 4.

Figure 6:
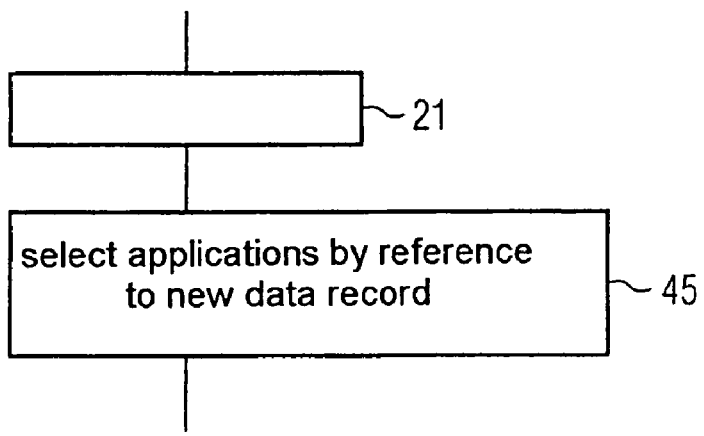

A possible way of determining the selected applications 2 is illustrated in FIG. 6. According to FIG. 6, a step 45 is executed directly after the step 21, that is to say even before the step 22 in FIG. 3 is executed. In this step 45, the central management component 9 selects the applications 2 by reference to the new data record 8. It therefore determines the selected applications 2 automatically by reference to the second data record 8. Such automatic determination is possible in particular because the data records 8 usually also contain information as to which examinations have been carried out. By reference to the examinations which have been carried out, the central management component 9 is then able to determine which applications 2 it is appropriate to use.

Figure 7:
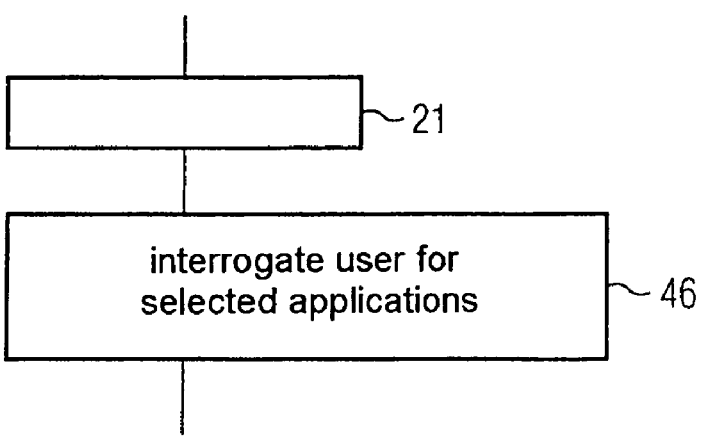

Alternatively, according to FIG. 7, it is also possible to interrogate the user with respect to the selected applications 2 in a step 46 directly after the step 21. In this case, the selected applications 2 of the central management component 9 are therefore predefined by the user 3 via the user interface 4.

Figure 8:
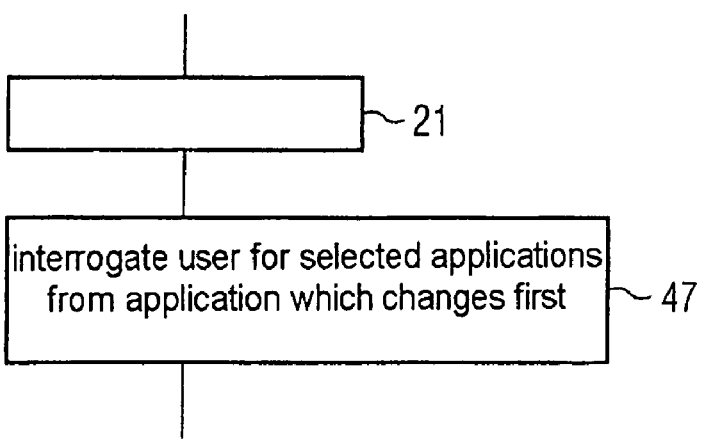

Alternatively, according to FIG. 8, the application 2 can also interrogate the selected applications 2 in a step 47, directly after the step 21, to determine which application 2 first loads the data 7 of the new data record 8, that is to say changes over the data record 8. In this case, the selected applications 2 of the central management component 9 are predefined by the application 2 which first loads data 7 of the new data record 8.

The applications 2 which are to be selected can be determined in various ways within the scope of the application 2 which first loads data 7 from the new data record 8. For example, according to FIG. 9 it is possible for the respective application 2 to firstly interrogate the list 10 of applications 2 from the central management component 9 in a step 48. The central management component 9 then transfers the list 10 to the calling application 2. The respective application 2 can therefore determine the applications 2 to be selected in a step 49 with reference to the new data record 8—likewise in the way already described basically for the central management component 9.

Alternatively it is also possible for the user 3 to be informed of the list 10 by the application 2 and then to allow the selection to be made by the user 3 in a step 50 which is indicated only by dashed lines in FIG. 9. In this case, the selected applications 2 are therefore predefined by the user 3 via the user interface 4.

As also illustrated in FIG. 9, the selected applications 2 are generally transferred to the central management component 9 in a step 51. The management component 9 then transfers the activation commands to the selected applications 2 in step 25, see FIG. 3. However, it is alternatively also possible to execute a step 52 which is indicated by dashed lines in FIG. 9. In step 52, the application 2 which first changes over the data record 8 transfers the activation commands itself to the selected applications 2.

Information indicating which applications 2 are to be selected always is preferably stored in the central management component 9. It is possible, for example, to store information in the central management component 9 which indicates that a reporting application (electronic patient record) is always selected. In this case, as indicated by dashed lines in FIG. 3, a step 53 is carried out between steps 24 and 25. In this step, the applications 2 which are to be selected always (for example the aforementioned reporting application) are selected.

If the transfer of the activation commands takes place by way of the application 2 which changes over the data record 8, the step 25 is also modified. In this case, the central management component 9 transfers only the activation commands for the additionally selected, that is to say preset, applications 2 to the application 2.

According to an embodiment of the present invention, the processing method therefore makes it possible for data 7 of the same data record 8 always to be processed at the front end (computer 1) and nevertheless for a targeted selection of the required applications 2 to be possible, the necessary management expenditure for this being minimal.

Exemplary embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A processing method for data combined to form a plurality of data records, using a plurality of applications, comprising:
   executing the applications quasi-simultaneously via a single computer;
   processing data, assigned to a first data record, via the applications at one time; and
   determining a changeover from the first data record to a second data record has occurred when data of the second data record is loaded into one of the applications, wherein the changeover is determined by a central management component and indicates a second data record is loaded into one of the applications;
   storing a list of the applications; and
   causing the other applications to terminate the processing of the data of the first data record in response to the determined changeover, and
   wherein at least descriptions of the functionalities executed by the applications are also stored in the list,
   wherein, when there is the changeover from the first data record to the second data record, an activation command is transferred to selected applications of the applications, on the basis of which activation command the data of the second data record is to be processed and the nonselected applications do not begin to process data of the second data record.

2. The processing method as claimed in claim 1, wherein descriptions of interfaces of the applications are also stored in the list.

3. The processing method as claimed in claim 2, wherein the applications sign on at the management component when the applications start and sign off when the applications end.

4. The processing method as claimed in claim 2, wherein the central management component determines the selected applications automatically by reference to the second data record.

5. The processing method as claimed in claim 2, wherein the selected applications of the central management component are predefined by a user via s user interface.

6. The processing method as claimed in claim 2, wherein the selected applications of the central management component are predefined by the application which first loads data of the second data record.

7. The processing method as claimed in claim 1, wherein the applications sign on with the central management component when the applications start and sign off when the applications end.

8. The processing method as claimed in claim 1, wherein the applications are at least one of entered into the list, and removed from the list by a user of the computer, via a user interface.

9. The processing method as claimed in claim 1, wherein a central management component determines the selected applications automatically by reference to the second data record.

10. The processing method as claimed in claim 1, wherein the selected applications of the central management component are predefined by a user via a user interface.

11. The processing method as claimed in claim 1, wherein the selected applications of the central management component are predefined by the application which first loads data of the second data record.

12. The processing method as claimed in claim 11, wherein the selected applications of the application which first loads data of the second data record are predefined by a user via a user interface.

13. The processing method as chimed in claim 12, wherein the activation command is transferred to the selected applications via a central management component.

14. The processing method as claimed in claim 12, wherein the activation command of the application which first loads data of the second data record is transferred to the selected applications.

15. The processing method as claimed in claim 1, wherein the activation command is transferred to the selected applications via the central management component.

16. The processing method as claimed in claim 1, wherein the activation command of the application which first loads data of the second data record is transferred to the selected applications.

17. The processing method as claimed in claim 1, wherein the information indicating which applications are to be selected always is stored in the central management component.

18. The processing method as claimed in claim 1, wherein the central management component is embodied as a work flow manager.

19. The processing method as claimed in claim 1, wherein the central management component stores the list of applications and on request, the central management component transfers the list of applications to the application which first loads data of the second data record.

20. The processing method as claimed in claim 1, wherein the data records are person-specific, medical data records.

21. A computer program product including executable instructions, which when executed by a computer cause the computer to perform a method comprising:
   executing the applications quasi-simultaneously via a single computer;
   processing data, assigned to a first data record, via the applications at one time; and
   determining a changeover from the first data record to a second data record has occurred when data of the second data record is loaded into one of the applications, wherein the changeover is determined by a central management component and indicates a second data record is loaded into one of the applications;
   storing a list of the applications; and causing the other applications to terminate the processing of the data of the first data record in response to the determined changeover, and wherein at least descriptions of the functionalities executed by the applications are also stored in the list, wherein, when there is the changeover from the first data record to the second data record, an activation command is transferred to selected applications of the applications, on the basis of which activation command the data of the second data record is to be processed and the nonselected applications do not begin to process data of the second data record.

22. A computer program product storing executable instructions, which when executed by a computer executing a plurality of applications, cause the computer to perform a method comprising:

receiving an indication that an application previously processing a first data record has loaded a second data record for processing;

determining a changeover has occurred in response to the loading of the second data record by the application, the changeover indicating the second data record is loaded into the application;

forming, at a central management component, a list of the applications processing the first data record; and causing the applications included in the list to terminate the processing of data of the first data record in response to the determined changeover wherein, when there is the changeover, an activation command is transferred to applications in the list of applications and other applications of the plurality of applications do not begin to process data of the second data record.

23. The computer program product as claimed in claim 22, wherein the formed list includes descriptions of the functionalities executed by the applications and interfaces of the applications.

24. A computer comprising:

a central management component configured to determine a changeover from a first data record to a second data record has occurred when data of the second data record is loaded in one of a plurality of applications previously processing data of the first data record, and to cause other applications of the plurality of applications to terminate processing of data of the first data record, wherein the changeover indicates the second data record is loaded in one of the plurality of applications, and when there is the changeover from the first data record to the second data record, an activation command is transferred to selected applications of the plurality of applications based on data of the second data record to be processed, and the nonselected applications do not begin to process data of the second data record.

25. The computer as claimed in claim 24, wherein the central management component stores a list of the plurality applications and at least descriptions of functionalities executed by the applications are stored in the list.

26. The computer as claimed in claim 24, wherein the central management component determines the selected applications automatically by reference to the second data record.

27. The computer as claimed in claim 24, wherein the selected applications of the central management component are predefined by the application which first loads data of the second data record.

* * * * *